United States Patent [19]

Schmitt et al.

[11] 3,953,517

[45] Apr. 27, 1976

[54] PROCESS FOR PREPARING METHYL ISOBUTYL KETONE AND CATALYST

[75] Inventors: Karl Schmitt; Josef Disteldorf; Werner Flakus, all of Herne; Werner Hubel, Wanne-Eickel, all of Germany

[73] Assignee: Veba-Chemie Aktiengesellschaft, Gelsenkirchen-Buer, Germany

[22] Filed: July 10, 1973

[21] Appl. No.: 377,979

Related U.S. Application Data

[63] Continuation-in-part of Ser. No. 756,997, Sept. 3, 1968, abandoned.

[30] Foreign Application Priority Data

Sept. 8, 1967 Germany............................ 1643044

[52] U.S. Cl. .......................... 260/593 R; 252/466 R
[51] Int. Cl.² ......................................... C07C 49/04
[58] Field of Search ................................ 260/593 R

[56] References Cited

UNITED STATES PATENTS

| 3,405,178 | 10/1968 | Wollner et al. ................. 260/593 R |
| 3,574,763 | 4/1971 | Wollner et al. ................. 260/593 R |
| 3,666,816 | 5/1972 | Takagi et al. .................. 260/593 R |

*Primary Examiner*—Bernard Helfin
*Assistant Examiner*—James H. Reamer
*Attorney, Agent, or Firm*—Burgess, Dinklage & Sprung

[57] ABSTRACT

Methyl isobutyl ketone is produced in a one-step process by contacting acetone and hydrogen at a temperature of from about 50°–200°C and a pressure between 50–100 atm, preferably 60–100 atm, in the presence of a catalyst composed of a cation exchange resin having from 0.001 to 0.1 weight percent of a noble metal distributed in monoatomic form therein.

5 Claims, 1 Drawing Figure

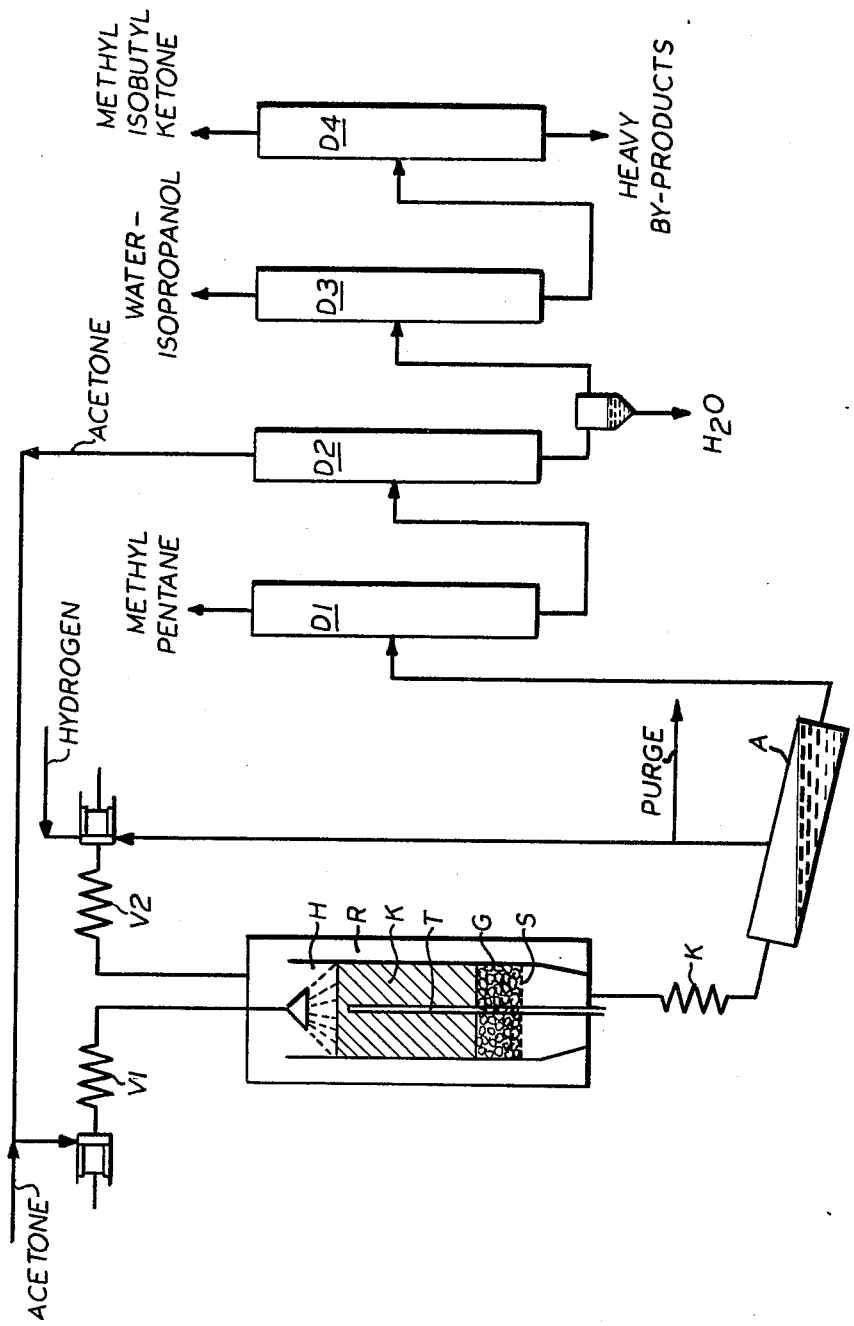

PROCESS FOR PREPARING METHYL ISOBUTYL KETONE AND CATALYST

RELATED APPLICATION

This application is a continuation-in-part of copending application Ser. No. 756,997, filed Sept. 3, 1968 now abandoned.

BACKGROUND

A number of methods for the manufacture of methyl isobutyl ketone from acetone and from isopropanol have long been known. Most of the processes known hitherto involve a number of stages. For example, acetone is reacted in the presence of basic condensation catalysts to form a diacetone alcohol, which, after concentration by distillation, is dehydrated by means of suitable catalysts (e.g., phosphoric acid). The mesityl oxide that is thus formed then has to be selectively hydrogenated in another stage of the process to methyl isobutyl ketone.

Strongly acid catalyst, including strongly acid cation exchangers, are used for the direct transformation of acetone to mesityl oxide.

Also known is a vapor phase process, in which methyl isobutyl ketone along with relatively large amounts of diisobutyl ketone can be produced from isopropanol in a single process stage. The catalyst is a mixed catalyst made of copper oxide, magnesium oxide and pumice flour. The transformations and yields are unsatisfactory.

According to another proposal, the three reaction steps (condensation, dehydration and selective hydrogenation) are combined in a single process stage, an alkaline catalyst being used for the condensation, in conjunction with a palladium-containing hydrogenation catalyst. The yields achieved are comparatively poor.

Another one-stage process for the manufacture of methyl isobutyl ketone is performed preferentially in a liquid phase in the presence of a mixture of a strongly acid cation exchanger and a hydrogenation catalyst working selectively on the olefinic double bond, at temperatures of 100° to 150°C, and in the presence of hydrogen. For the continuous performance of the proposal, it is proposed that acetone be sprayed over a solid catalyst made of a mixture of the two catalysts, with a counter-current of hydrogen. Such a solid catalyst can be obtained by compressing equal parts by weight of cation exchanger and 5% palladium on charcoal. Investigation has shown, however, that a combination catalyst prepared in this manner has a completely insufficient mechanical stability. Due to the great differences in the swelling capacity of such ion exchanger resins in relation to water and acetone, briquettes of this kind are rapidly destroyed by slight loading variations, whether due to irregular sprinkling or due to changes in the rate of transformation. Furthermore, the amount of palladium required is very high in comparison to the process of the invention.

SUMMARY

It has now been found that an outstandingly suitable catalyst with low noble metal concentrations for the single-stage one-step manufacture of methyl isobutyl ketone from acetone and hydrogen at pressures of 50–100 atm, preferably 60–100 atm, can be obtained very simply by first chemically binding a noble metal — preferably palladium — in cationic form to an ion exchanger that is preferably already in the H+ form, and then thoroughly washing the exchanger and reducing it with hydrogen, whereupon the noble metal ions are converted to the monoatomic, metallic form. The chemical reactions that take place can be formulated as follows:

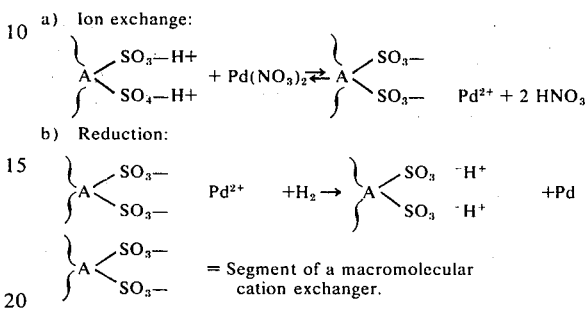

= Segment of a macromolecular cation exchanger.

DESCRIPTION OF THE DRAWING

The present invention will more fully be understood from the following description taken in conjunction with the accompanying drawing which is a schematic flow diagram of apparatus suitable for carrying out the process of the invention for preparing methyl isobutyl ketone.

DESCRIPTION

Suitable ion exchangers are especially the strongly acid cation exchangers on a basis of polystyrene-divinylbenzene. Whereas, on account of the high sulfur content of such exchanger resins (8 to 20% S in the dry substance), a great deactivation of the metallic palladium might have been expected, it was surprising to observe a high hydrogenation activity along with an especially good selectivity.

These two properties are probably explained by the special manner in which the noble metal is applied to the support substance, whose function is here performed by the exchanger resin. Due to the exchange of the noble metal ions for the H+ or Na+ ions of the ion exchanger, and the associated fixation in the resin, a substantially monoatomic distribution of the nobel metal ions is obtained, which is preserved in the reduction that follows. On account of the high activity of such a catalyst, extremely low concentrations of noble metal are sufficient on a weight basis. Thus, the catalyst according to the invention for preparing methyl isobutyl ketone from acetone and hydrogen is a cation exchange resin having from 0.001–0.1 weight percent noble metal in monoatomic form distributed therein. The preferred catalyst has from 0.001 to 0.08 weight percent noble metal distributed in the cation exchange resin and highly preferred catalysts have from 0.05 to 0.08 weight percent noble metal distributed in the resin. The preferred ranges for the noble metal in the catalyst described herein are preferred for the reason that methyl isobutyl ketone can be prepared in high yields with the formation of very small amounts of undesirable byproducts. Compare the results in Examples 1 and 3 of the present application with the by-products formed in Examples 1 and 2 of U.S. Pat. No. 3,574,763, issued Apr. 13, 1971.

The effects herein indicated become especially plain when an exchanger resin having a macroporous structure is used (e.g., Lewatit SP 120, Amberlyst 15, Amerlite 200). (Capitalization of material names indicates trademarks.)

The manufacture of the catalyst according to the invention is characterized by great simplicity. The absorption of the palladium ions from aqueous solution is virtually complete. The reduction, i.e., the transformation of the noble metal ions ionically linked to the macromolecular network of the exchanger resin to the neutral atoms takes place rapidly, even at room temperature and at low hydrogen partial pressures (under 1 atm). The mechanical stability of the exchanger resin is in no way impaired, so that the catalyst can be subjected even to extreme loading variations. Additional characteristics are excellent resistance to attrition and great resistance to breakdown under repeated drying and wetting.

The catalyst according to the invention can be used in batch processes and in continuous processes, including sprinkling processes using co-current and counter-current hydrogen flow, flooding processes and gaseous-phase processes. Preference, however, must be given to the sprinkling process in which the acetone to be reacted is fed downward through the catalyst bed and a current of hydrogen is passed through the reaction zone in the same direction, on account of the yield and the simplicity of its technology. In this process the catalyst can be arrranged in a shaft furnace or in a tube furnace in a cohering layer. The use of a tube exchanger as the reactor system permits a better removal of the reaction heat and makes possible a virtually isothermal management of the reaction. If a shaft furnace is used, the reaction heat can be absorbed by excess hydrogen.

Due to the high activity of the catalyst according to the invention, the hydrogenation starts even at comparatively low temperatures; on the other hand, its high selectivity also permits the use of higher temperatures, with the net result of a greater freedom as regards temperature. The range that is of interest for the performance of the reaction is between 50° and 200°C, preferably between 80° and 150°C.

High hydrogen pressures are advantageous both for reasons of the kinetics of the reaction and for reasons relating to the technology of the process, and they can be used on account of the high selectivity of the catalyst described without any diminution of the yield due to the formation of methyl isobutyl carbinol and isopropanol. The acetone and reaction product losses are furthermore lower. On the other hand, however, even at very low hydrogen partial pressures (e.g. 1 atm and lower), the intermediately developing mesityl oxide can still be sufficently hydrogenated.

According to the invention methyl isobutyl ketone is prepared from hydrogen and acetone at pressures in the range of 50 to 100 atm. The preferred pressure range is between about 60 and about 100 atm. The higher pressure range of 60–100 atm. is preferred because higher yields of methyl isobutyl ketone are realized when working within the preferred pressure range. Compare Examples 1–3 herein with the yield in Example 4 herein. It should be noted that the process described herein is unique in that it combines extremely low catalyst concentrations with high reaction pressures which results in a highly desirable end result, namely, extremely high yields of methyl isobutyl ketone with extremely low by-product formation. These features can be readily appreciated by comparing the amounts of by-products formed and the yields of methyl isobutyl ketone demonstrated in Examples in this application with the results set forth in U.S. Pat. No. 3,574,763.

The acetone throughput can be widely varied in the sprinkling process. Throughputs of 5 volume units of acetone per volume unit of catalyst per hour result in transformations that are still economically tolerable.

The formation of by-products is prevented to a great extent by the use of the catalyst of the invention. In particular, the formation of fatty acids (acetic acid, isobutyric acid), which have an adverse effect on the condensation process itself and on the distillative purification of the reaction product, is suppressed. The emerging reaction product has acid numbers of less than 0.04 mg KOH/g. The occurrence of such low acid contents is probably due to the fact that the mesityl oxide level can be kept extremely low throughout the reaction time. Mesityl oxide is known to be easily liable to hydrolytic cleavage. In like manner, the formation of other by-products, such as isobutylene, methyl pentane, methyl pentene, methyl isobutyl carbinol, diisobutyl ketone, 4,6-dimethylheptanone-(2) and higher ketones is kept so low that yields of 96% and more can be achieved.

EXAMPLE 1

40 liters of Lewatit SP 120 ion exchange resin, $H^+$ form, is poured into a solution of 50 g of palladium nitrate $(Pd(NO_3)_2 \cdot 9 H_2O)$ in 20 liters of distilled water. After about 1 hour the palladium has been entirely absorbed by the exchanger. The resin is separated from the aqueous solution by decantation and washed repeatedly with water. Then it is reduced in a suitable vessel (which has been thoroughly scavenged with nitrogen) with hydrogen at room temperature and atmospheric pressure. The catalyst thus prepared contains 0.05% Pd.

A sleeve H made of V2A (stainless steel) having an inside diameter 155 mm is inserted into a high-pressure reaction tube R made of steel and having an inside diameter of 160 mm, in such a manner that it is sealed off at the bottom against the outer tube (see drawing). In the bottom of the sleeve there is a fine-mesh screen S of V2A, on which a bed of glass balls G 20 mm thick is laid, followed by the catalyst K. Also in the reactor is a centrally located thermometer tube capable of receiving as many as 7 resistance thermometers set at various desired levels.

40 liters per hour of acetone is pumped onto the catalyst after being warmed to 80°C by a steam-heated foreheater (VI). At the same time, hydrogen is fed cocurrently through the reactor by means of a circulating compressor, the reactor being under total pressure of 60 atmospheres gauge. At the same time, the hydrogen being circulated is preheated in another foreheater V2 so that a temperature of 80°C develops at the upper end of the catalyst zone, while at the output of the reactor a temperature of 135°C is maintained by controlling the quantity of the circulating gas (corresponding to 20 to 25 normal cubic meters per hour). After emerging from the reactor, the circulating gas and reaction product pass together into a condenser (K) and are separated at 50°–60°C in a separator. The reaction product is delivered to apparatus for distillative purification. In a first column D1 the methylpentane forming as a by-product is removed (boiling temperature of the acetone-methylpentane azeotrope: 47°C; 44 wt-% acetone, 56 wt-% methylpentane). At D2 the unreacted acetone is distilled off and fed back to the reactor. An aqueous phase can be separated from the sump product and discarded. At the head of column D3, the water and isopropanol dissolved in the organic phase are removed. Finally, in D4 the pure methyl isobutyl ketone is drawn off at the head, while in the sump the more greatly condensed reaction products (diisobutyl ketone, etc.) collect, together with small amounts of mesityl oxide and methyl isobutyl carbinol.

A gas-chromatographic analysis of the product running into column D1 shows the following composition:

| | | |
|---|---|---|
| Acetone | 65.85 | wt-% |
| Isopropanol | 0.03 | wt-% |
| Methyl pentane | 0.12 | wt-% |
| Methyl pentene | 0.003 | wt-% |
| Methyl isobutyl ketone | 28.35 | wt-% |
| Mesityl oxide | 0.004 | wt-% |
| Methyl isobutyl carbinol | 0.01 | wt-% |
| Diisobutyl ketone | 0.65 | wt-% |
| 4,6-dimethylheptanone-(2) | 0.16 | wt-% |
| Higher-boiling products (after distillation) | 0.05 | wt-% |
| Water (KF titration) | 5.6 | wt-% |

Accordingly, an acetone transformation of 34.4% is computed, and a yield of 96.5% with reference to reacted acetone.

The catalyst showed no diminution of performance after 105 days of operation. On a basis of experimental hydrogenations in a smaller apparatus, a life of 1.5 to 2 years can be expected.

EXAMPLE 2

The experimental apparatus described in Example 1 is used with the same catalyst, and the throughput is increased to 80 l/h. At the same time the maximum reaction temperature is raised to 140°C. An acetone transformation of 29.5% is obtained and a yield of 97.1%.

EXAMPLE 3

10 liters of Amberlite 200 ion exchange resin, H+ form, is prepared as described in Example 1 in such a manner as to achieve a palladium content of 0.08% (i.e., 20 g Pd (NO$_3$)$_2$ . 9 H$_2$O). The finished catalyst is poured into a tube reactor, consisting of 7 tubes having a diameter of 26 mm and a length of 4 m. The outer jacket has a diameter of 150 mm. The entire reactor is made of high-grade steel. The heat of reaction is removed through an evaporative cooler under pressure, with tap water as the medium. At the upper part of the reactor is a distribution cup having saw-toothed overflow tubes, which provides for a uniform action on the acetone.

The catalyst is uniformly distributed to the individual tubes of the reactor, thus filling them to a depth of 2700 mm.

40 liters of acetone per hour, preheated to 135°C, is pumped into the distribution cup of the reactor. Hydrogen is metered in according to consumption, so that a total pressure of 100 atmospheres gauge is maintained. By means of a level control, tap water is fed to the cooling chamber in the bottom part, while steam is removed from the upper part by means of a pressure regulator (2.9 atm, 132°C). The reaction product is carried from the lower tube chamber through a condenser into a gas separator whose gas chamber is connected to the reactor by a pressure equalizing line. The liquid phase collected in the separator is continuously distilled (cf. Example 1). The gas-chromatographic analysis shows the following composition in the reaction porduct:

| | | |
|---|---|---|
| Acetone | 74.40 | wt-% |
| Isopropanol | 0.031 | wt-% |
| Methyl pentane | 0.102 | wt-% |
| Methyl pentene | — | |
| Methyl isobutyl ketone | 19.91 | wt-% |
| Mesityl oxide | — | |
| Methyl isobutyl carbinol | 0.02 | wt % |
| Diisobutyl ketone | 0.265 | wt-% |
| 4,6-dimethylheptanone-(2) | 0.061 | wt-% |
| Higher-boiling products (after distillation) | 0.05 | wt-% |
| Water (KF titration) | 4.16 | wt-% |

From this an acetone transformation of 24.2% is computed, and a yield of 97.4% with reference to reacted acetone.

EXAMPLE 4

In the same manner as in Example 3, 10 liters of acetone are brought to reaction per hour at a reaction temperature of 145°C at 50 atmospheres total gauge pressure. A yield of 95.8% is obtained, with an acetone transformation of 45.9%.

As stated above, the preferred noble metal is palladium. Any of the noble metals known in the prior art to be suitable for use in combination with cation exchange resins for the reaction of the invention can be used.

What is claimed is:

1. In a process for preparing methyl isobutyl ketone from acetone and hydrogen the improvement which comprises contacting hydrogen and acetone in the presence of a catalyst at a temperature of from about 50°-200°C and a pressure between 60 and 100 atmospheres, said catalyst being a cation exchange resin having 0.001 to 0.08 weight percent noble metal in monoatomic form distributed therein.

2. Process of claim 1 wherein said catalyst is prepared by reducing a cation exchange resin containing noble metal cations to reduce noble metal and deposit noble metal in monoatomic form in said resin.

3. Process of claim 1 wherein the noble metal is palladium.

4. In a process for preparing methyl isobutyl ketone from acetone and hydrogen, the improvement which comprises contacting hydrogen and acetone in the presence of a catalyst at a temperature of from about 50° to about 200°C and a pressure between 60 and 100 atmospheres, said catalyst being a cation exchange resin having from 0.05 to 0.08 weight percent noble metal in monoatomic form distributed therein.

5. Process of claim 4 wherein said noble metal is palladium.

* * * * *